US00PP36614P2

(12) United States Plant Patent
Gómez Porras et al.

(10) Patent No.: US PP36,614 P2
(45) Date of Patent: Apr. 22, 2025

(54) OLIVE TREE NAMED 'I 99'

(50) Latin Name: *Olea europaea*
Varietal Denomination: I 99

(71) Applicant: TODOLIVO S.L., Cordova (ES)

(72) Inventors: Jose María Gómez Porras, Cordova (ES); Luis Rallo Romero, Cordova (ES); Diego Barranco Navero, Cordova (ES); Concepción Muñoz Diez, Cordova (ES); Carlos Trapero Ramírez, Cordova (ES); Pedro Valverde Caballero, Cordova (ES)

(73) Assignee: TODOLIVO S.L., Cordova (ES)

( * ) Notice: Subject to any disclaimer, the term of this patent is extended or adjusted under 35 U.S.C. 154(b) by 0 days.

(21) Appl. No.: 18/445,921

(22) Filed: Mar. 27, 2024

(51) Int. Cl.
*A01H 5/08* (2018.01)
*A01H 6/00* (2018.01)

(52) U.S. Cl.
USPC ..... Plt./158

(58) Field of Classification Search
USPC ..... Plt./158
CPC ..... A01H 5/08; A01H 5/00; A01H 6/00
See application file for complete search history.

(56) References Cited

U.S. PATENT DOCUMENTS

PP19,511 P2 12/2008 Navero et al.

OTHER PUBLICATIONS

Boletin del Registro de Variedades Protegidas No. 2/2021 for Olivo I 99, retrieved on Jul. 24, 2024 at https://www.mapa.gob.es/ministerio/pags/Biblioteca/Revistas/pdf_RVP%2FRVP-2-2021.pdf, pp. 1, 8. (Year: 2021).*

Upov Pluto Jul. 23, 2024 for Olea I 99, retrieved on Jul. 24, 2024 at https://pluto.upov.int/result, p. 1. (Year: 2024).*

* cited by examiner

*Primary Examiner* — June Hwu
(74) *Attorney, Agent, or Firm* — Hunt IP Law

(57) ABSTRACT

The new and distinct variety of olive tree variety 'I 99' is provided. The variety can be distinguished by its outstanding features of low vigor. high yield, and high oil content.

3 Drawing Sheets

Latin name of the genus and species:
Botanical classification:
a. Genus—*Olea.*
b. Species—*europaea.*
Variety denomination: The new olive tree claimed is of the variety denominated 'I 99'.

BACKGROUND OF THE INVENTION

Field of the Invention

The present invention relates to a new and distinct variety of olive tree, which has been given the variety denomination of '199'.

BACKGROUND OF THE RELATED ART

Olive oil continues to increase in popularity. Accordingly, there is a continuing need to develop new and improved olive oils to meet the increased demand for use in various food types and in cooking. Many olive varieties are self-sterile. As a result, there is a need for the development of new olive varieties which are self-pollination and produce a high yield of new and improved olive oil for commercialization.

SUMMARY OF THE INVENTION

The present invention relates to a new and distinct variety of olive tree, which has been given the variety denomination of '199'. '199' is intended for use for oil production.

The new olive tree variety is a selection resulting from a sexual cross of olive trees at Córdoba, Spain in 2008, involving a seed parent known as 'Arbosana' (unpatented) and a pollen parent known as 'Chiquitita' (U.S. Plant Pat. No. 19,511 P2).

The selection was subsequently evaluated for a number of years at Córdoba, Spain.

Asexual reproduction of the new variety by cutting propagation since 2008 at Córdoba, Spain has demonstrated that the new variety reproduces true to type with all of the morphological characteristics, as herein described, firmly fixed and retained through successive generations of such asexual propagation.

Selection criteria were low vigor, high yield, and high oil content.

Plants of the new variety differ from plants of the seed parent 'Arbosana' primarily in vigor and growth habit, with low vigor and a spreading to drooping growth habit, while Arbosana has a higher vigor and an open growth habit. Plants of the new variety differ from plants of the pollen parent 'Chiquitita' primarily in growth habit, the new variety having spreading to drooping growth habit and 'Chiquitita' having a drooping habit. This new variety stands out for its high production compared to its parents 'Arbosana' and 'Chiquitita', with a higher oil production level than both parents, between 15-20%. Additionally, this variety is notable for its low vigor. This variety produces fruit with medium weight which are colored dark violet at full maturity.

Plants of the new variety differ from the varieties mentioned in co-pending applications Ser. No. 18/445,924 (for Olive Tree Variety Named 'I 100') and Ser. No. 18/445,929 (for Olive Tree Variety Named 'I 101'). Each of the varieties, 'I-99', 'I-100', and 'I-101', come from the same parents so their growth habit is similar. The new variety differs in the color of the fruit at full maturity, with a black color as opposed to the dark violet of 'I-100'. The new variety differs in the growth habit, with a spreading to drooping habit as opposed to the drooping habit of 'I-101'.

BRIEF DESCRIPTION OF THE DRAWINGS

The accompanying photographic illustrations show the typical appearance of the new variety 'I 99'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
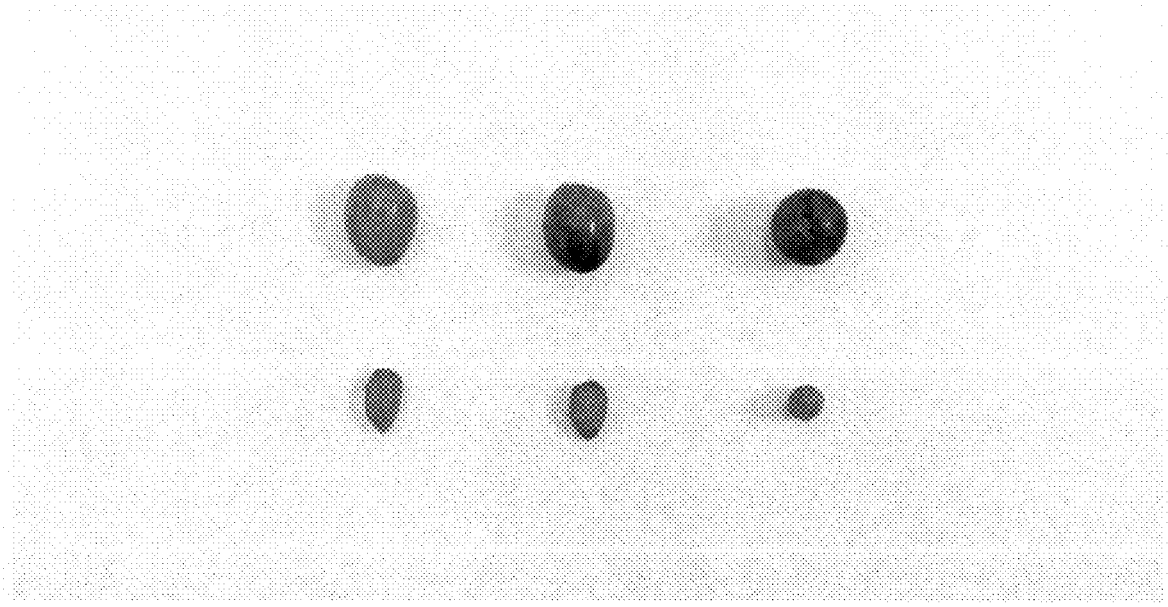
FIG. 1 is a photograph of the new variety 'I 99', demonstrating fruits and stones. Left and center depict the side view. Right depicts stalk end view.
Figure 2:
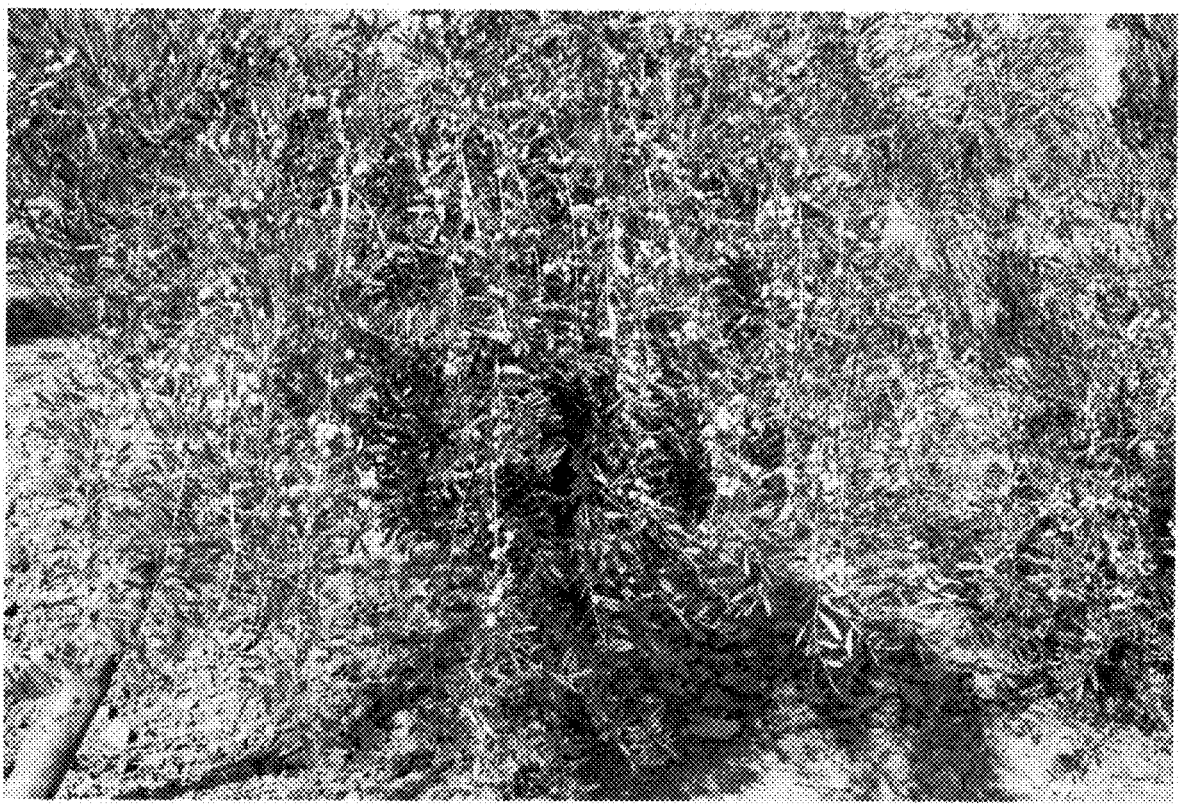
FIG. 2 is a photograph of the new variety 'I 99', demonstrating fruit, fruit color, and branching habit.
Figure 3:
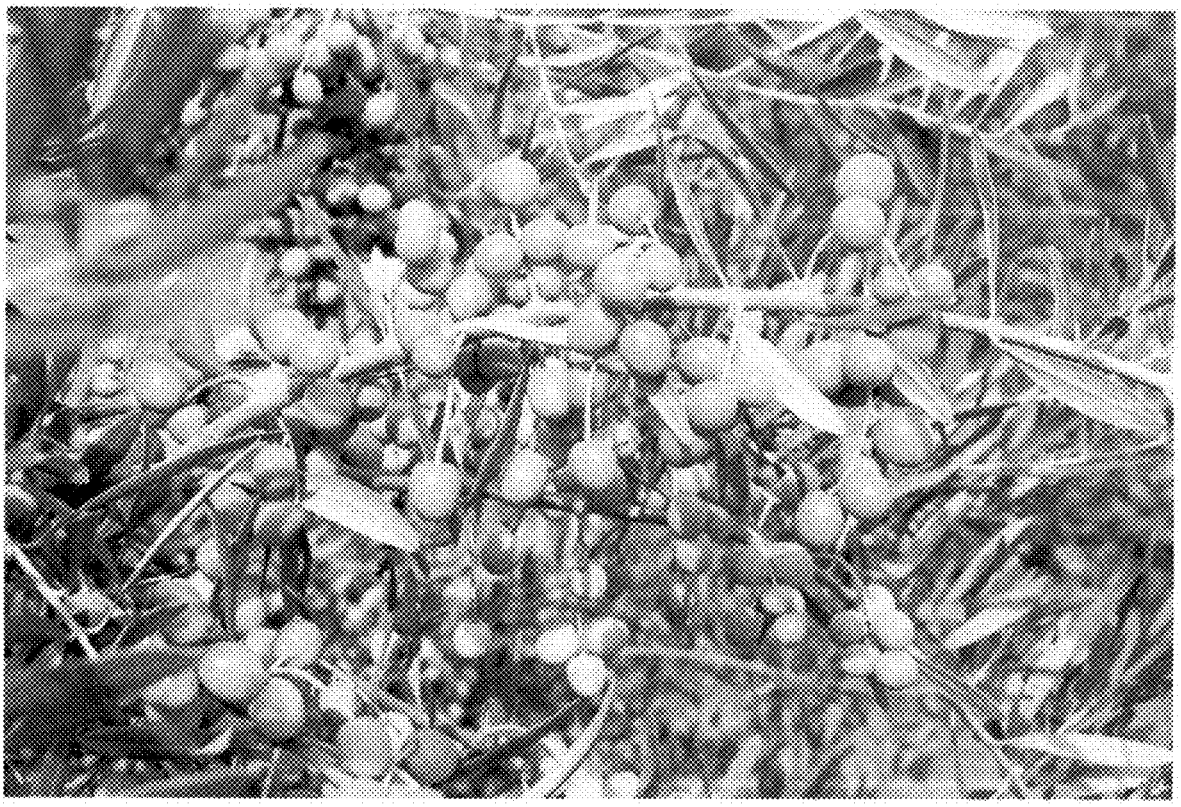
FIG. 3 is a photograph of the new variety 'I 99', demonstrating fruit and fruit color.

The following detailed description sets forth the distinctive characteristics of 'I 99'. The datum which defines these characteristics was collected from asexual reproductions of the original selection. Dimensions, sizes, colors, and other characteristics are approximations and averages set forth as accurately as possible. The plant history was taken on plants approximately 5 years and 8 months of age, and the descriptions relate to plants grown in Córdoba, Spain. Color notations are in reference to the standard Color Chart is that of The Royal Horticultural Society (R.H.S. Colour Chart, 2015 edition. London, England).

Classification:

a. *Latin name.*—*Olea europaea* L.
b. *Common name.*—Olive tree.
c. *Variety name.*—'I 99'.

Parentage:

a. *Female parent.*—'Arbosana' (unpatented).
b. *Male parent.*—'Chiquitita' (U.S. Plant Pat. No. 19,511 P2).

PLANT

General:

a. *Height.*—230 cm (average).
b. *Width.*—110 cm (average).
c. *Growth habit.*—Spreading.
d. *Vigor.*—Low-medium.
e. *Tree canopy density.*—Medium.

ROOTS

General:

f. *Rooting habit.*—Normal-Dense
g. *Texture.*—Fibrous.
h. *Color designation* (*young roots*).—155A.
i. *Color designation* (*old roots*).—157A.

STEMS

General:

j. *Branching habit.*—Spreading.
k. *Trunk.*—i. Circumference — 7 cm. ii. Surface texture — Smooth. iii. Color — 199A.
l. *Main stems.*—i. Quantity — Dependent on the management and pruning. ii. Aspect — Smooth. iii. Strength — Robust. iv. Cross-section — Rounded Small. v. Circumference — 6 cm (diameter) at 50 cm. vi. Surface texture (young stems) — Smooth. vii. Surface texture (mature stems) — Smooth with lenticels. viii. Color designation (young stems) — 157A. ix. Color designation (mature stems) — 157B. x. Lenticels — Many, 1 mm long, 0.5 mm wide. xi. Internode length — Ranging from 5-12 cm.
m. *Lateral branches.*—i. Quantity — Abundant. ii. Cross-section — Oval. iii. Length — 80-180 cm. iv. Internode length — Ranging from 2-3 cm. v. Texture — Smooth with raised lenticels. vi. Aspect — Outward. vii. Strength — Flexible. viii. Color (young lateral branches) — 196D. ix. Color (mature lateral branches) — 197D. x. Pubescence — None.

FOLIAGE

General:

n. *Arrangement.*—Opposite.
o. *Attachment.*—Petiolate
p. *Division.*—Simple.
q. *Curvature.*—Straight.
r. *Lamina.*—i. Length — 60 mm (average). ii. Width — 10 mm (average). iii. Thickness — 1.5-2 mm. iv. Shape — Acuminate. v. Aspect — Straight. vi. Apex — Acuminate. vii. Base — Cuneate. viii. Margin — Entire (smooth). ix. Texture of upper surface — Smooth. x. Texture of lower surface — Slightly pubescent. xi. Color of young lamina (upper surface) — 141B. xii. Color of young lamina (lower surface) — 142B. xiii. Color of mature lamina (upper surface) — 143B. xiv. Color of mature lamina (lower surface) — 142B. xv. Venation pattern — Pinnate.
s. *Petiole.*—i. Length — 2 mm. ii. Diameter — 1.2 mm. iii. Texture — Smooth. iv. Strength — Medium. v. Color — 142B.

INFLORESCENCE

General:

t. *Type.*—Panicle.
u. *Natural flowering season.*—Spring.
v. *Flowering habit.*—1-10 days during May.
w. *Length.*—2.5-6.5 cm.
x. *Width.*—1-3 cm.
y. *Quantity of florets per inflorescence.*—20-25.
z. *Peduncle.*—i. Length — 2.5-6.5 cm. ii. Width — 1.2 cm. iii. Texture — Smooth. iv. Strength — Medium. v. Color — 141D. vi. Diameter — 1.2 cm.
aa. *Pedicels.*—i. Length — 2 mm. ii. Width — 1 mm. iii. Texture — Smooth. iv. Strength — Medium. v. Color — 141D.

FLOWER BUD

General:

bb. *Shape.*—Globular.
cc. *Length.*—2-4 mm.

dd. *Width.*—2 mm.
ee. *Color.*—157A.

FLOWER

General:
ff. *Type.*—Perfect.
gg. *Shape.*—Cruciform.
hh. *Persistence.*—Medium.
ii. *Fragrance.*—Smooth and intoxicating.
jj. *Diameter.*—3-6 mm.
kk. *Height.*—2-3 mm.
ll. *Calyx.*—i. Quantity of sepals — 4. ii. Arrangement — Rotate. iii. Diameter — 1 cm.
mm. *Sepals.*—i. Sepal fusion — Fused. ii. Length — 1 mm. iii. Width — 1 mm. iv. Shape — Bell shape. v. Apex — Obtuse. vi. Base — Cuneate. vii. Margin — Entire. viii. Texture — Smooth. ix. Color (upper surface) — 149A. x. Color (lower surface) — 149A.
nn. *Petals.*—i. Arrangement — Rotate. ii. Quantity — 4. iii. Fusion — Sympetalous petals fused at the proximal half of the corolla. iv. Shape — Acute. v. Apex — Acute. vi. Base — Cuneate. vii. Margin — Entire. viii. Texture — Smooth. ix. Color when opening (upper surface) — NN155D. x. Color when opening (lower surface) — NN155D. xi. Color when fully opened (upper surface) — NN155D. xii. Color when fully opened (lower surface) — NN155D. xiii. Color fading — Not fading.

REPRODUCTIVE ORGANS

General:
oo. *Androecium.*—i. Stamen quantity — 2. ii. Filament length — Approximately 0.75 mm. iii. Filament color — 130B. iv. Anther attachment — Basifixed. v. Anther shape — Hemispherical. vi. Anther size — 1 mm. vii. Anther color — 2A. viii. Abundance of pollen — Abundant. ix. Pollen color — 2A.
pp. *Gynoecium.*—i. Pistil quantity — 1. ii. Stigma shape — Bifid cone shape. iii. Stigma length — Approximately 0.75 mm. iv. Stigma color — 145D. v. Style size — Approximately 0.75 mm. vi. Style color — 145D. vii. Ovary position — Superior. viii. Ovary shape — Round. ix. Ovary diameter — Approximately 0.75 mm. x. Ovary color — 145D.

SEED AND FRUIT

General:
qq. *Fruit.*—i. Date of maturity — November-December. ii. Size — Medium. iii. Weight — 1.50 g (medium). iv. Diameter — 12.5 mm (medium). v. Length — 15 mm (medium). vi. Form — Ovoidal. vii. Suture — None. viii. Stem cavity — Medium. ix. Stem — Medium. x. Caliper — Medium. xi. Apex — Rounded. xii. Pistil point — Obscure. xiii. Skin thickness — Less than 1 mm. xiv. Skin texture — Smooth. xv. Skin tendency to crack — None. xvi. Skin color — 83A. xvii. Flesh color — 158C. xviii. Pit color — 144C. xix. Oil/juice production — Oil production higher when compared to other commercial cultivars, including 'Arbequina', 'Arbosana', and 'Koroneiki' in the organoleptic properties, polyphenol content, and stability. xx. Flavor — Different/Excellent. xxi. Ripening — Medium. xxii. Nipple Intensity — Absent. xxiii. Color at full maturity — 202A.
tt. *Stone.*—i. Quantity — 1. ii. Shape — Ovate. iii. Type — Slightly asymmetric. iv. Fibers — None. v. Weight — 0.25 g (medium). vi. Length — 14 mm (medium). vii. Width — 7 mm (medium). viii. Thickness — 7 mm. ix. Apex — Rounded. x. Base — Truncate. xi. Color — 162B. xii. Texture — Slightly grooved. xiii. Mucron — Present. xiv. Suture — Present. xv. Sides — Acute. xvi. Ridges — Round. xvii. Tendency to split — None. xviii. Number of grooves on basal end — between 7 and 10. xix. Distribution of grooves on basal end — weakly grouped around suture.

DEVELOPMENT

General:
a. *Flowering season.*—1-10 days during May.
b. *Harvesting season.*—7 months from flowering to harvest.
c. *Time to produce a fruit bearing tree.*—3 years.
d. *Chilling requirements.*—Average/typical for olives.
e. *Plant/fruit disease resistance.*—i. Repilo (*Cycloconium oleaeginea*) — Resistant. ii. *Verticillium* (*Verticillium dahliae*) — Resistant. iii. Tuberculosis (*Pseudomonas savastanoi*) — Tolerant.
f. *Fruit market use.*—Oil with intense fruitiness and apple-green color. It has aromas of banana, apple and hints of almond shells. It is sweet and balanced on the palate, slightly bitter and slightly spicier.
g. *Fruit yield.*—1,000 grams of oil per plant.
h. *Hardiness zone* (*heat/cold resistance*).—Zone 9b: −3.9° C. to −1.1° C.

The new variety 'I 99' has not been observed under all possible environmental conditions to date. Accordingly, it is possible that the phenotypic expression may vary somewhat with changes in light intensity and duration, cultural practices, and other environmental conditions.

The invention claimed is:

1. A new and distinct variety of olive tree named 'I 99', as illustrated and described herein.

* * * * *